(12) United States Patent
Shaw et al.

(10) Patent No.: US 12,268,848 B2
(45) Date of Patent: Apr. 8, 2025

(54) SYRINGE WITH FLAT INDICIA DISPLAY SURFACE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 15/940,305

(22) Filed: Mar. 29, 2018

(65) Prior Publication Data

US 2019/0298928 A1    Oct. 3, 2019

(51) Int. Cl.
*A61M 5/31*    (2006.01)
*A61M 5/32*    (2006.01)

(52) U.S. Cl.
CPC ........ *A61M 5/3129* (2013.01); *A61M 5/3221* (2013.01); *A61M 2005/3126* (2013.01); *A61M 2005/3227* (2013.01)

(58) Field of Classification Search
CPC ........ A61M 5/50; A61M 5/178; A61M 5/321; A61M 5/322; A61M 5/3129; A61M 5/3205; A61M 5/3221; A61M 5/3232; A61M 2005/314; A61M 2005/3125; A61M 2005/3126; A61M 2005/3227; A61M 2205/586

See application file for complete search history.

(56) References Cited

U.S. PATENT DOCUMENTS

| | | | |
|---|---|---|---|
| 2,117,469 | A | 5/1938 | Woodyatt |
| 2,860,635 | A * | 11/1958 | Wilburn ................. A61M 5/28 |
| | | | 604/190 |
| 4,573,976 | A | 3/1986 | Sampson et al. |
| 4,650,468 | A | 3/1987 | Jennings, Jr. |
| 4,702,738 | A | 10/1987 | Spencer |
| 4,790,828 | A | 12/1988 | Dombrowski et al. |
| 4,840,619 | A | 6/1989 | Hughes |
| D302,726 | S | 8/1989 | Schwobel |
| 4,915,696 | A | 4/1990 | Feimer |

(Continued)

FOREIGN PATENT DOCUMENTS

| | | |
|---|---|---|
| CN | 102068734 A | 5/2011 |
| CN | 102573959 A | 7/2012 |

(Continued)

OTHER PUBLICATIONS

Machine translation of Dragosits et al DE 4323466 A1 (Year: 1994).*
Machine translation of FR2809627A1 (Year: 2000).*

*Primary Examiner* — Laura A Bouchelle
(74) *Attorney, Agent, or Firm* — Scheef & Stone, LLP; Robin L. Barnes; Mike Schofield (57) ABSTRACT

A medical syringe having a barrel with a substantially cylindrical, longitudinally extending fluid chamber, a needle retraction cavity substantially coextensive in length with the fluid chamber and disposed adjacent and parallel to the fluid chamber, and at least one substantially flat, outwardly facing display area configured to receive and display an array of volumetric measuring indicia in alignment with and proximal to the fluid chamber.

41 Claims, 8 Drawing Sheets

(56) References Cited

U.S. PATENT DOCUMENTS

| | | |
|---|---|---|
| 4,946,447 A | 8/1990 | Hardcastle et al. |
| 4,994,034 A * | 2/1991 | Botich ................ A61M 5/5013 |
| | | 604/110 |
| 5,037,402 A | 8/1991 | Bartman |
| 5,049,133 A | 9/1991 | Villen Pascual |
| 5,053,010 A | 10/1991 | McGary et al. |
| 5,084,018 A | 1/1992 | Tsao |
| 5,092,461 A | 3/1992 | Adam |
| 5,215,534 A | 6/1993 | DeHarde et al. |
| 5,312,372 A | 5/1994 | DeHarde et al. |
| 5,407,436 A | 4/1995 | Toft et al. |
| 5,437,647 A | 8/1995 | Firth et al. |
| 5,445,618 A | 8/1995 | Adobbati |
| 5,456,668 A | 10/1995 | Ogle, II |
| D377,687 S | 1/1997 | Udovch |
| 5,672,161 A | 9/1997 | Allen et al. |
| 5,782,804 A | 7/1998 | McMahon |
| D420,129 S | 2/2000 | McMahon |
| 6,090,077 A | 7/2000 | Shaw |
| 6,213,987 B1 | 10/2001 | Hirsch et al. |
| 6,416,323 B1 | 7/2002 | Grenfell et al. |
| 6,585,690 B1 * | 7/2003 | Hoeck ................ A61M 5/3234 |
| | | 604/218 |
| D601,242 S | 9/2009 | Bierman et al. |
| D601,243 S | 9/2009 | Bierman et al. |
| 9,044,552 B2 | 6/2015 | Schraga |
| 9,173,726 B2 | 11/2015 | Sabourin |
| 9,308,353 B1 | 4/2016 | Shaw et al. |
| 9,381,309 B2 | 7/2016 | Shaw et al. |
| 9,623,192 B2 | 4/2017 | Chin et al. |
| D792,969 S | 7/2017 | Taylor |
| 9,814,841 B2 | 11/2017 | Shaw et al. |
| D812,748 S | 3/2018 | Funakoshi et al. |
| D814,630 S | 4/2018 | Finke et al. |
| D815,732 S | 4/2018 | Mills et al. |
| D817,482 S | 5/2018 | Howell et al. |
| 9,956,352 B2 | 5/2018 | Shaw et al. |
| D823,457 S | 7/2018 | Shaw et al. |
| D823,461 S | 7/2018 | Shaw et al. |
| D823,463 S | 7/2018 | Shaw et al. |
| D829,891 S | 10/2018 | Shaw et al. |
| 10,086,141 B2 | 10/2018 | Steel et al. |
| 10,525,207 B2 * | 1/2020 | Zivkovic ............. A61M 5/3202 |
| 10,568,554 B2 | 2/2020 | Shaw et al. |
| 10,625,028 B2 | 4/2020 | Shaw et al. |
| 11,000,217 B2 | 5/2021 | Shaw et al. |
| D923,463 S | 6/2021 | Krauss |
| 11,141,570 B2 | 10/2021 | Shaw et al. |
| 11,246,989 B1 | 2/2022 | Halbach |
| 2002/0065488 A1 | 5/2002 | Suzuki et al. |
| 2002/0068907 A1 * | 6/2002 | Dysarz ................ A61M 5/3232 |
| | | 604/191 |
| 2002/0082560 A1 | 6/2002 | Yang |
| 2003/0028171 A1 | 2/2003 | DeHarde |
| 2003/0038171 A1 | 2/2003 | Lim et al. |
| 2005/0020988 A1 * | 1/2005 | Woehr ................ A61M 5/3234 |
| | | 604/243 |
| 2005/0159706 A1 | 7/2005 | Wilkinson et al. |
| 2006/0084925 A1 * | 4/2006 | Ramsahoye ...... A61M 5/31525 |
| | | 604/218 |
| 2007/0276338 A1 | 11/2007 | Shue et al. |
| 2008/0114306 A1 | 5/2008 | Bare |
| 2012/0004621 A1 | 1/2012 | Shaw et al. |
| 2012/0022464 A1 | 1/2012 | Zivkovic et al. |
| 2013/0023826 A1 | 1/2013 | Ishida |
| 2014/0012206 A1 * | 1/2014 | Shaw ................ A61B 5/150587 |
| | | 604/198 |
| 2015/0073303 A1 | 3/2015 | Shaw et al. |
| 2015/0196714 A1 * | 7/2015 | Creaturo ........... A61M 5/31526 |
| | | 604/218 |
| 2015/0202373 A1 | 7/2015 | Creaturo |
| 2015/0231335 A1 | 8/2015 | Creaturo |
| 2022/0054764 A1 | 2/2022 | Shaw et al. |
| 2023/0034986 A1 | 2/2023 | Shaw et al. |
| 2024/0075216 A1 | 3/2024 | Shaw et al. |
| 2024/0165337 A1 | 5/2024 | Shaw et al. |
| 2024/0165341 A1 | 5/2024 | Shaw |

FOREIGN PATENT DOCUMENTS

| | | | |
|---|---|---|---|
| CN | 104368068 A | 2/2015 | |
| CN | 108619594 A | 9/2018 | |
| DE | 4323466 A1 * | 1/1994 | .......... A61M 5/3129 |
| FR | 2809627 A1 * | 12/2001 | ............ A61M 5/322 |
| JP | 2010098323 | 2/2010 | |
| JP | 2016529078 | 9/2016 | |
| WO | 2013050475 | 4/2013 | |
| WO | 2016055620 A1 | 4/2016 | |
| WO | WO-2016176523 A1 * | 11/2016 | .......... A61M 5/3129 |

* cited by examiner

SYRINGE WITH FLAT INDICIA DISPLAY SURFACE

BACKGROUND OF THE INVENTION

1. Field of the Invention

This invention relates to a syringe configured for medical use in aspirating or injecting fluids. The syringe desirably includes a barrel, a plunger slidably engaging a portion of the barrel, a forwardly projecting, needle and a substantially flat indicia display surface disposed on the barrel. One aspect of the invention is a barrel having a laterally offset needle retraction cavity that is substantially coextensive with the length of the fluid chamber of the barrel. The substantially full-length, laterally offset needle retraction cavity facilitates the optional use of longer retractable needles than are usable with conventional safety syringes having retractable needles and broadens the range of uses and procedures that are performable with the device without increasing the overall length of the syringe. Depending upon needle length, such uses and procedures can include, for example, performing spinal taps, administering epidural anesthesia, aspirating cysts, and the like, as well as for administering intradermal, subcutaneous or intramuscular injections.

Another aspect of the invention relates to a syringe having a barrel comprising a substantially cylindrical fluid chamber, a needle retraction cavity disposed in parallel and laterally spaced-apart relation to the fluid chamber, and at least one substantially flat, outwardly facing display surface to which indicia such as dosage scales can be applied using a conventional pad printing process. Still another aspect of the invention relates to a syringe having a barrel with two oppositely facing, substantially flat surfaces on which the same or different indicia can be pad printed without having to rotate the barrel, even when printing on 1 mL, 0.5 mL or smaller syringes. The substantially flat display surfaces also facilitate the application of indicia to a syringe by other processes such as embossing, injection molding, and the like.

Another aspect of the invention relates to a medical syringe comprising a barrel and plunger as disclosed above in combination with a frontal attachment having a forwardly projecting, rearwardly biased needle. The frontal attachment and barrel are desirably cooperatively configured so that the frontal attachment slidably engages a front portion of the barrel along an axis that is transverse to the longitudinal axis through the needle.

2. Description of Related Art

Syringes intended for medical use typically have barrels comprising substantially cylindrical inside and outside walls, meaning that volumetric dosage indicia or other markings are applied to an arcuate outer surface during manufacture. This can be difficult, and especially so when the diameter of the barrel and radius of curvature of the outside wall are small (as with 1 mL, 0.5 mL and smaller syringes) and where the available outside surface area is extremely limited, or on syringes where different dosing scales or other indicia are applied to opposite sides of the barrel. In such instances it is often necessary to spin or rotate the barrel while printing, and it is also often difficult to read indicia such as dose measuring lines and the related numeric values or other markings because they wrap so far around the circumference of the barrel and because indicia or markings on one side are often viewable through the syringe and can confuse the user, sometimes leading to the commission of medical errors. For at least these reasons, syringes having substantially flat surfaces for use in applying dosage markings and other indicia are needed.

Medical syringes having rearwardly biased needles that retract into coaxially aligned retraction cavities disposed inside the plunger are known, having previously been disclosed, for example, in U.S. Pat. Nos. 5,049,133; 5,053,010; 5,084,018 and 6,090,077. More recently, medical syringes having frontal attachments containing rearwardly biased needles that retract into needle retraction cavities that are part of the frontal attachment have been disclosed, for example, in U.S. Pat. No. 9,381,309.

Even more recently, medical syringes with frontal attachments have been disclosed that slidably engage barrels having needle retraction cavities unitarily molded together with the barrel and disposed parallel to the fluid chamber. In U.S. Pat. No. 9,814,841 (FIGS. 37-42), for example, the length of the needle retraction cavity is substantially shorter than the length of the fluid chamber inside the barrel and the needle retraction cavity does not cooperate with an outer wall of the barrel to form substantially flat outside surfaces that are adjacent to and substantially coextensive with the fluid chamber.

SUMMARY OF THE INVENTION

A syringe for medical use is disclosed that comprises a one-piece barrel having a fluid chamber and a laterally offset needle retraction cavity that are substantially parallel and separated by a common wall. The needle retraction cavity can have a non-circular cross-section and is desirably substantially coextensive in length with the fluid chamber, thereby facilitating the use of longer needles without increasing the overall length of the barrel in order to accommodate retraction of the longer needles as is the case with safety syringes that retract the needle into the barrel following use. The barrel further comprises an outer wall having at least one substantially flat, outwardly facing display surface upon which indicia such as a volumetric dosage scale, for example, can be applied using conventional pad printing technology or another similarly effective alternative means. The at least one substantially flat display surface is desirably disposed proximally to the fluid chamber and also desirably comprises a measurement scale that is longitudinally aligned with at least that portion of the fluid chamber that is useful for injecting or aspirating a fluid. According to one preferred embodiment of the invention, two oppositely facing, longitudinally coextensive, substantially flat surfaces are provided, with each surface spanning at least a portion of an external wall of the fluid chamber and at least a portion of the external wall of the needle retraction cavity.

The subject invention is particularly useful with syringes having usable volumes of 1 mL or less, which syringes typically have smaller barrel diameters that cause the volumetric dosage indicia applied to the outside surface to wrap around a greater portion of the circumference of the barrel. According to another preferred embodiment of the invention, pad printing technology (sometimes referred to as "tampography") is used to apply volumetric dosage indicia or other markings to the substantially flat display surface of the syringe. The needle retraction cavity can be made (preferably molded from a suitable polymeric material) with a non-circular cross-section and is offset laterally from the barrel to facilitate creation of a wider, outwardly facing, substantially flat display surface during manufacture. The substantially flat display surface desirably comprises at least one side that is proximal to the fluid chamber of the barrel and thereby provides an opportunity, if desired, for molding volumetric dosage markings or other indicia onto the otherwise flat display surface or embossing the indicia on or into the display surface.

Another embodiment of the subject syringe comprises a barrel and plunger as disclosed above in combination with a frontal attachment having a forwardly projecting, rearwardly biased needle. The frontal attachment and barrel are desirably cooperatively configured so that the frontal attachment slidably engages a front portion of the barrel along an axis that is transverse to the longitudinal axis through the needle. When the syringe is disposed in the use position, the needle is aligned with a first opening in the front of the barrel that is communicates with a substantially cylindrical fluid chamber inside the barrel to establish a coaxially aligned fluid flow path between the fluid chamber and the needle. A fluid seal is desirably seated around the first opening to resist fluid leakage between the frontal attachment and the barrel. The needle retraction cavity extends rearwardly from a second opening in the front of the barrel in parallel and spaced-apart relation to the fluid chamber in the barrel, and desirably shares a common wall with at least a portion of fluid chamber. Following use of the syringe, relative transverse movement between the barrel and the frontal attachment repositions the rearwardly biased needle into alignment with the needle retraction cavity, thereby releasing the needle to be forced by the biasing means, typically a compressed spring, into a retracted position wherein the needle no longer projects forwardly from the syringe.

Another embodiment of the subject syringe embodies wider, substantially flat display surfaces disposed on a medical syringe having a unitary barrel and needle retraction cavity that cooperate with substantially flat edge portions of the surrounding flange to help prevent the syringe from rolling off a tray or other flat surface. The substantially flat surfaces also allow the flange around the barrel to be proportionally narrower as compared to the flanges of conventional syringes having tubular barrels and still provide larger surface areas that are more easily graspable by a user. The oppositely facing, substantially flat surfaces also improve stability and the degree of control that can be exercised over the syringe by a user during an injection or other procedure. Because the subject syringe has a barrel with a laterally offset needle retraction cavity that can be molded integrally with the fluid chamber, at least one, and preferably two (oppositely facing), substantially flat, outwardly facing surface areas are provided that are useful for the placement of an array comprising a volumetric scale or other indicia that are easily readable by the user and thereby reduce the likelihood of dosing errors during aspiration or injection.

Another embodiment of the invention comprises the subject syringe in combination with a selectively releasable needle cover that can also comprise a locking member configured to engage a portion of the barrel and resist sliding lateral movement of the barrel relative to the frontal attachment to prevent accidental retraction of the needle prior to using the syringe. Retraction of the needle following use of the syringe reduces the likelihood of reusing the syringe or of accidental needle sticks and the inadvertent transmission of blood-borne pathogens.

Another embodiment of the invention comprises the subject syringe in combination with a plunger cap that is releasably attached to the rear portion of the syringe, typically behind the finger flange, and is selectively removable prior to fluid aspiration or use. When both the needle cover and the plunger cap are in place, the needle and the internal, fluid-contacting portions of the syringe are enclosed and protected from contamination whether or not the syringe is also enclosed inside another package. Because of this, the syringes can be assembled and shipped in bulk prior to packaging and sterilization.

Although the subject syringe is especially useful in administering relatively small doses of a medicinal fluid such as insulin or a vaccine to a user by injection or infusion, the structure and operation of the apparatus is not limited to particular sizes, doses or procedures. For example, syringes configured as disclosed here can also be configured for use in aspirating fluid samples from patients during clinical procedures such as knee or spinal taps. Because the overall syringe length is reduced through use of the disclosed frontal attachment in combination with the novel barrel of the invention, longer needles can be used and still be retracted into the syringe following use. As used in this disclosure, "retracted" or "retraction" refer to the process by which a needle is moved from a forwardly projecting use position to a post-use position in which the needle point no longer projects forwardly from the frontal attachment, no matter whether the force acting upon the needle is pushing or pulling the needle tip rearwardly from the forwardly projecting position.

These and other features of the present invention will be better understood from a consideration of the following detailed description of various embodiments and appended claims in conjunction with the accompanying drawings.

BRIEF DESCRIPTION OF THE DRAWINGS

The syringe of the invention is further described and explained in relation to the following drawings wherein.

DESCRIPTION OF PREFERRED EMBODIMENTS

Figure 1:
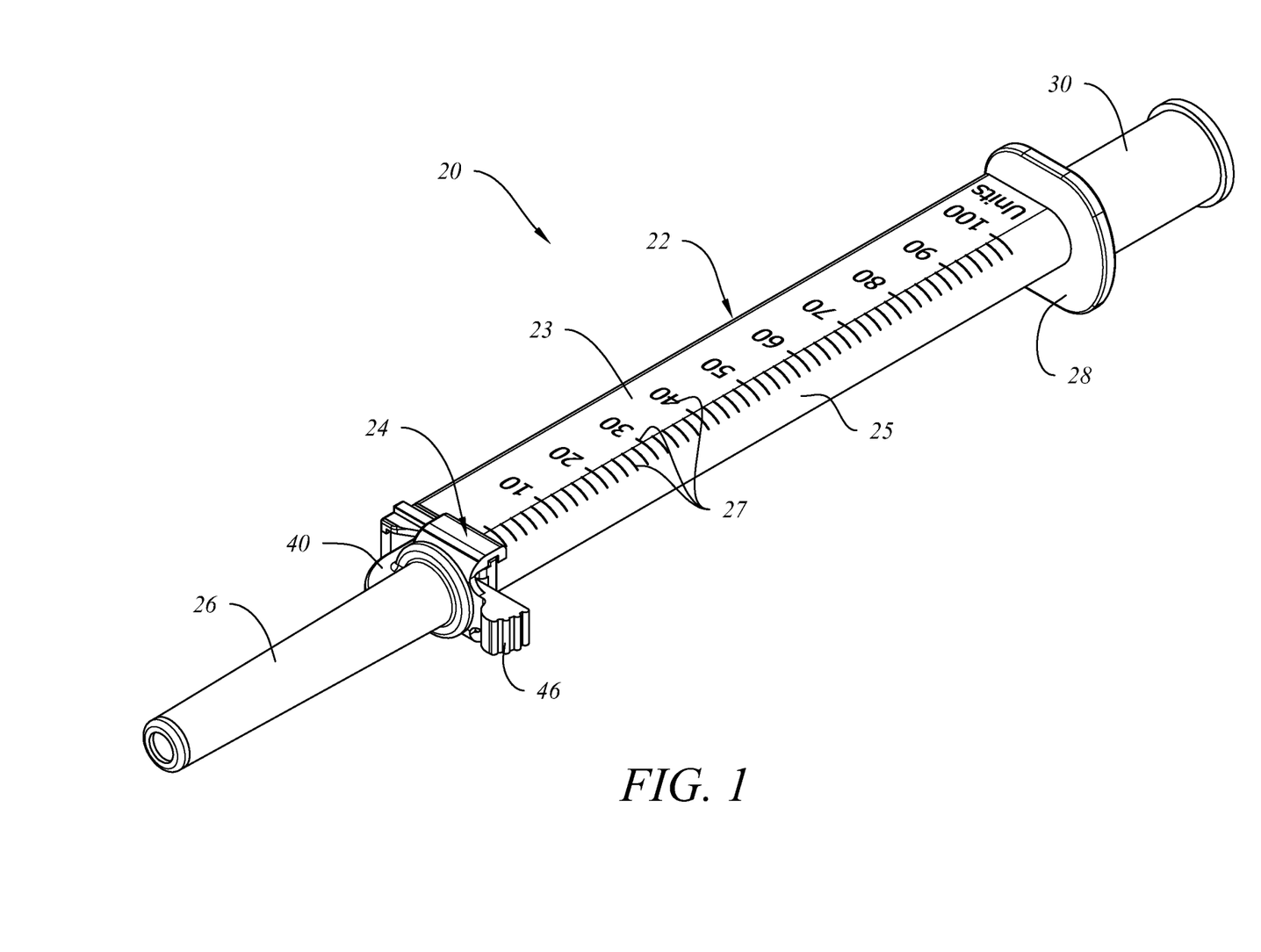
FIG. 1 is a top front perspective view of one embodiment of the invention in which the needle cover (including the locking member) and the plunger end cap are installed in the position in which the subject syringes can be packaged, shipped and stored, with the locking member of the needle cover restricting lateral sliding movement of the barrel relative to the frontal attachment prior to use.

Referring to FIG. 1, syringe 20 comprises barrel 22 further comprising substantially flat display surface 23, frontal attachment 24, outside wall 25 of fluid chamber 75 (visible in FIG. 9), selectively removable needle cover 26, an array of volumetric measuring indicia 27, finger flange 28, removable plunger cap 30 and locking member 40. As shown in FIG. 1, the principal volumetric measuring indicia 27 are applied to display surface 23, including for example at least the Arabic numerals identifying the number of fluid units and the associated principal measurement indicia. It should be appreciated, however, that the accompanying figures of the drawings are for illustrative purposes and are not drawn to scale and that placement of some features such as the secondary unit markings 27 relative to substantially flat display surface 23 can vary from the positions shown. At least a portion of each secondary (individual) unit indicia or markings desirably commences on display surface 23 or proximal to the edge of display surface 23, and optionally continues for a short distanced onto the curved outer wall of fluid chamber 25. Such placement is understood to be within the operational capabilities of conventional pad printing technology that is now readily available to those of ordinary skill in the art.

Figure 9:
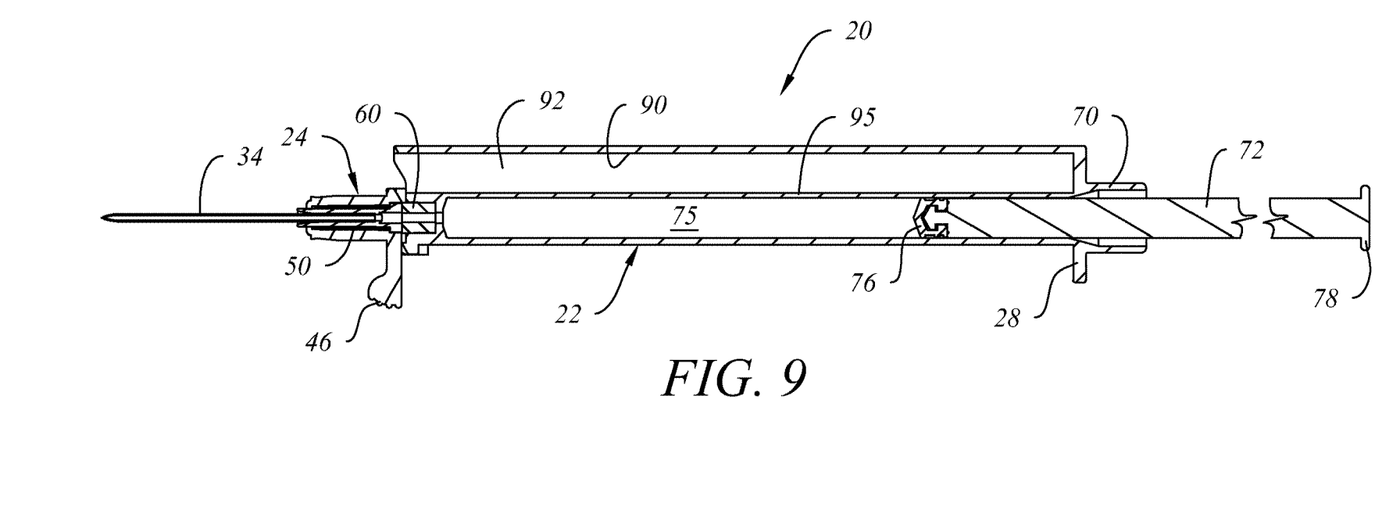
FIG. 9 is a cross-sectional view taken along line 9-9 of FIG. 8.

As depicted in FIG. 1, syringe 20 has frontal attachment 24 shown in the "pre-use" configuration with needle cover 26 and locking member 40 in place to prevent frontal attachment 24 from shifting laterally relative to barrel 22 prior to use because of pressure inadvertently applied to textured touch pad 46 or to the opposite side of barrel 22. Removable plunger cap 30 is also installed behind finger flange 28 to prevent the plunger (not visible) from being accidentally withdrawn from barrel 22 and to prevent inadvertent contamination inside the rear opening of barrel 22 or around the rearwardly extending handle portion of the plunger, as seen in FIG. 9, which is discussed below.

Figure 2:
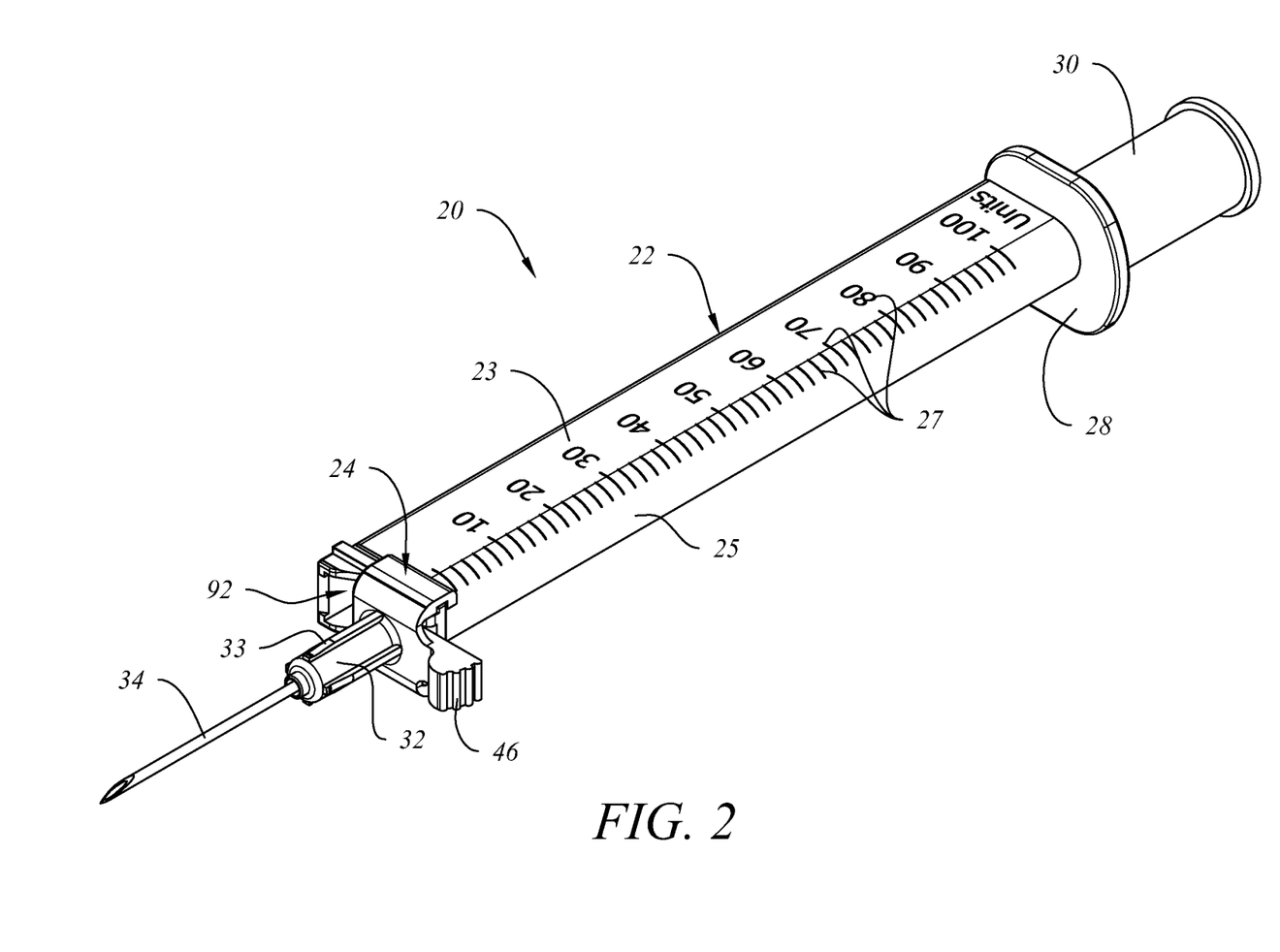
FIG. 2 is a top front perspective view of the embodiment of FIG. 1 in which the needle cover is removed.

Referring to FIGS. 2, 4-5 and 12, barrel 22 and frontal attachment 24 of syringe 20 are shown in the same position as in FIG. 1 except that needle cover 26 (with locking member 40) is removed. The front opening into needle retraction cavity 92 is more clearly visible, and needle 34 is also visible, projecting forwardly from needle support member 32 of frontal attachment 24. Circumferentially spaced, axially tapered ribs 33 are disposed around needle support member 32 and provide surfaces for frictional engagement with the inside surface of needle cover 26 prior to removal. In FIG. 2, needle 34 is desirably coaxially aligned with the longitudinal axis through fluid chamber 75 (FIG. 9).

Figure 3:
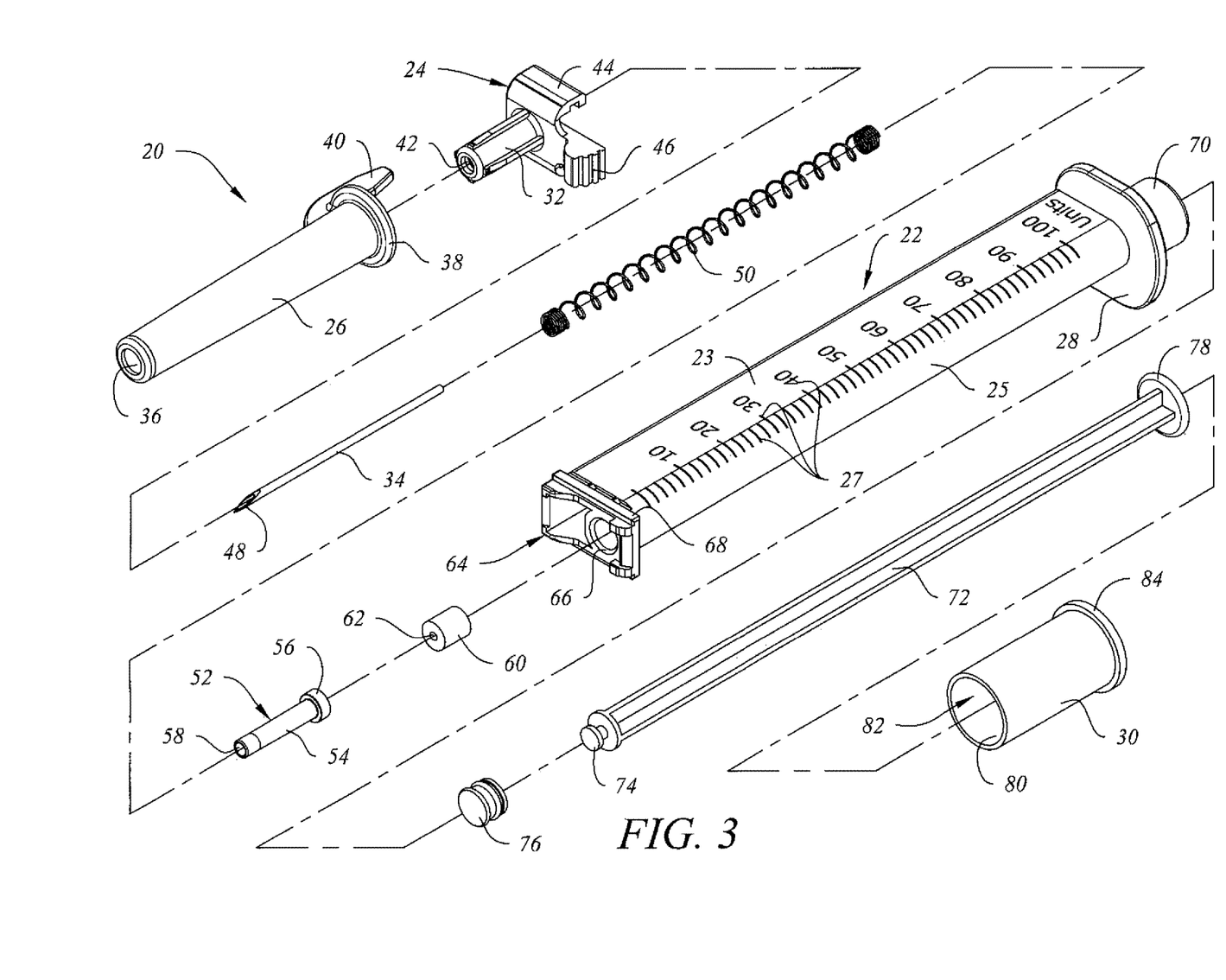
FIG. 3 is an exploded top front perspective view of the embodiment of FIG. 1.

Referring to FIG. 3, needle cap 26 of syringe 20 further comprises a forwardly facing, inwardly tapered, substantially cylindrical sidewall having front end 36, rearwardly facing annular collar 38, and locking member 40 projecting rearwardly past annular collar 38. Frontal attachment 24 further comprises forwardly projecting, substantially tubular needle support member 32 with front opening 42, upper guide member 44, lower guide member 45 (visible in FIG. 7), and laterally projecting textured touch pad 46.

Syringe 20 desirably includes needle 34 with forwardly facing beveled needle tip 48, and a needle retraction mechanism further comprising coiled compression spring 50 and needle holder 52. Needle holder 52 further comprises an elongated shaft 54 with tubular bore 58 that is insertable into the rear of spring 50. The diameter of head 56 of needle holder 52 is sufficiently greater than the inside diameter of spring 50 that spring 50 can be held in compression by head 56 when frontal attachment 24 is slidably engaged with front portion 64 of barrel 22 as discussed in relation to FIGS. 6 and 7 below. The rear end of needle 34 is insertable into tubular bore 58 of needle holder 52 and attachable in fixed relation to the inside of elongated shaft 54 by any suitable, commercially available means such as an adhesive. Although a needle retraction mechanism as disclosed here is satisfactory for use in syringe 20, it will be appreciated that other similarly effective elements and mechanisms useful for rearwardly biasing needle 34 inside syringe 20 can also be used in making the invention.

Still referring to FIG. 3, annular polymeric fluid seal 60 with tubular bore 62 is desirably insertable into recess 66 in front portion 64 of barrel 22 so that the forwardly facing end of seal 60 is disposed in abutting contact with rearwardly facing head 56 of needle holder 52 when the needle retraction mechanism is installed inside frontal attachment 24 and frontal attachment 24 is attached in slidable engagement with front portion 64 of barrel 22. When frontal attachment 24 of syringe 20 is assembled to front portion 64 of barrel 22 during manufacture, a continuous, substantially linear, fluid flow path is established through needle 34, needle holder 52 and annular fluid seal 60 into tubular, longitudinally extending fluid chamber 75 (visible in FIG. 9).

In addition to front portion 64, barrel 22 further comprises substantially flat display surface 23, curved outside wall surface 25, finger flange 28 and rearwardly projecting annular collar 70. During assembly of syringe 20, elastomeric plunger seal 76 is desirably installed on forwardly projecting boss 74 on the front end of plunger handle 72 opposite rearwardly facing plunger thumb pad 78, and plunger handle 72 is then inserted into a rearwardly facing opening defined by annular collar 70. Assembly of syringe 20 is then completed by installing substantially cylindrical plunger cap 30 on the rearwardly facing end of barrel 22. Plunger cap 30 further comprises open front end 80, cylindrical bore 82 and closed rear end 84. Plunger cap 30 is installed around plunger thumb pad 78 and in frictional engagement with the outside wall of annular collar 70. Volumetric measuring indicia 27 applied as discussed in relation to FIG. 1 also appear on the outwardly facing portions of substantially flat display surface 23 and curved outside wall surface 25.

Figure 6:
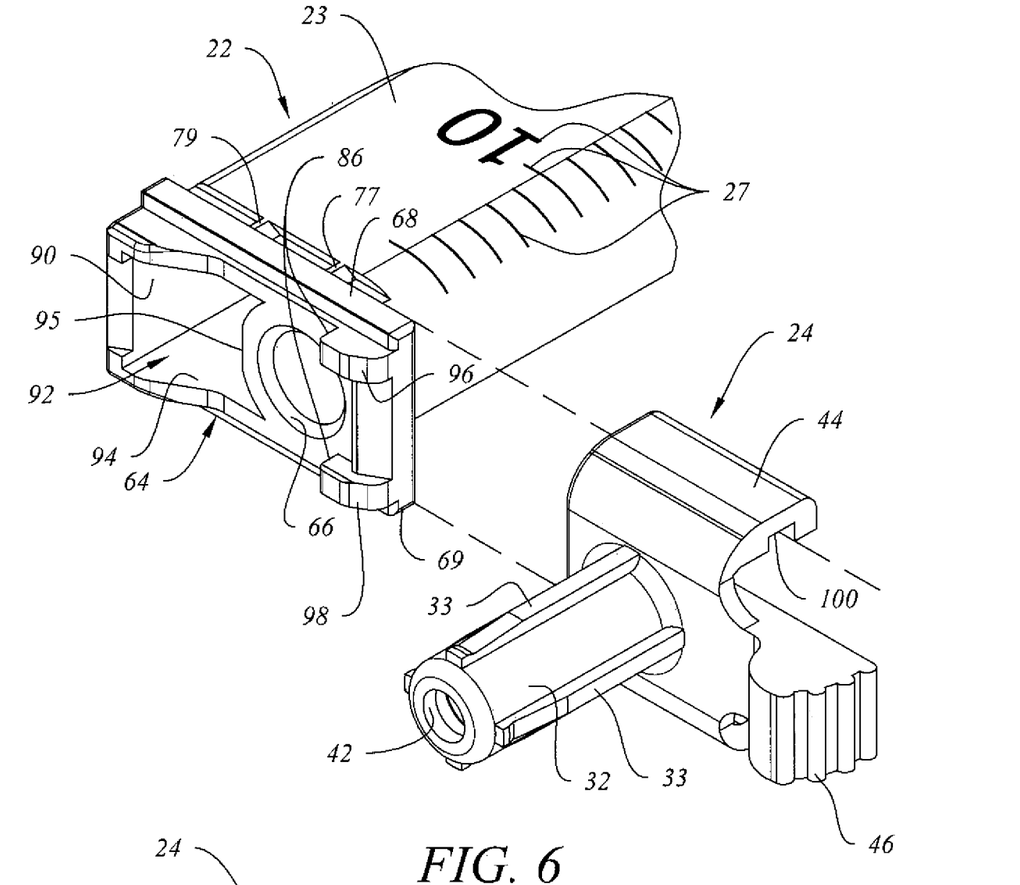
FIG. 6 is an exploded detail perspective view, partially broken away, of the frontal attachment of the embodiment of FIG. 3 shown in juxtaposition to the front portion of the barrel of the embodiment of FIG. 3.
Figure 11:
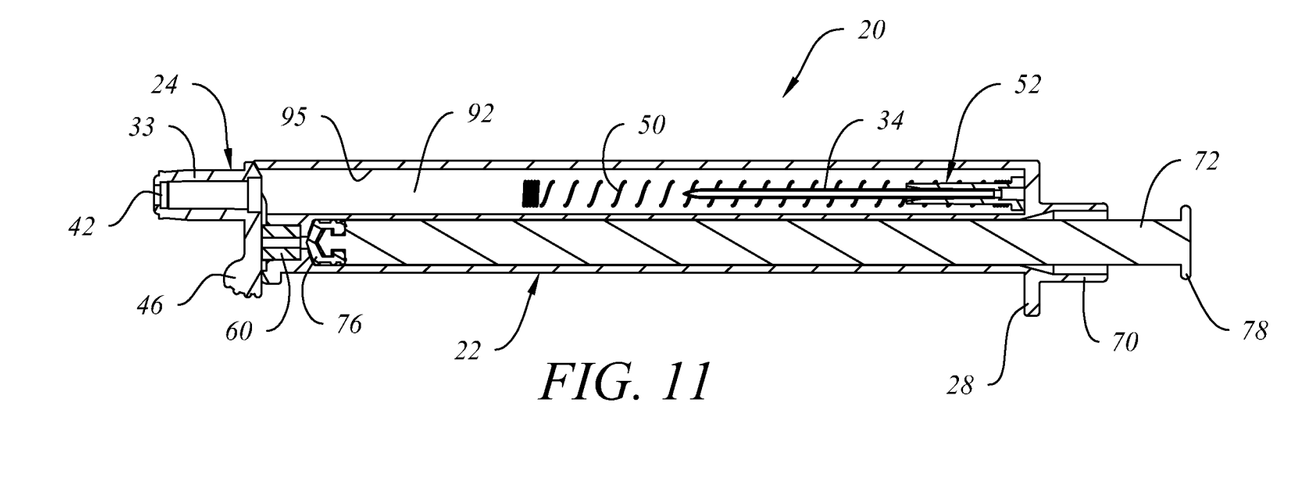
FIG. 11 is a cross-sectional view taken along line 11-11 of FIG. 10.
Figure 12:
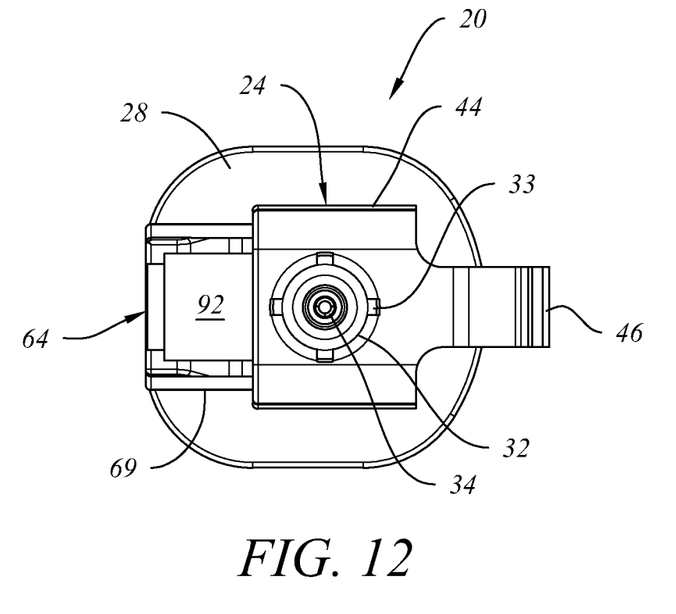
FIG. 12 is a front elevation view of the embodiment of FIG. 2.

FIGS. 3, 6 and 11 further disclose the forwardly facing opening into needle retraction cavity 92 in relation to front portion 64 of barrel 22. Needle retraction cavity 92 has a closed rear end that is adjacent to finger flange 28, and is bounded by side walls 90, 95, bottom wall 94, and a top wall that also includes upwardly facing, substantially flat display surface 23 of barrel 22.

Figure 7:
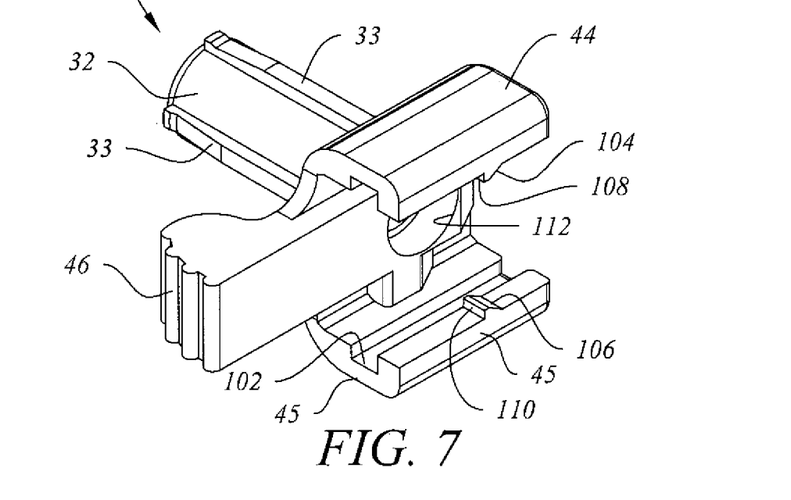
FIG. 7 is a top rear perspective view of the frontal attachment of FIG. 3.

The assembly of frontal attachment 24 to front portion 64 of barrel 22 of syringe 20 is further described and explained in relation to FIGS. 6 and 7. Referring to FIG. 6, annular fluid seal 60 (visible in FIG. 3) is first inserted into recess 66 of front portion 64 of barrel 22. Front portion 64 further comprises laterally extending top rail 68 and bottom rail 69 that are disposed in transverse relation to the longitudinal axis through fluid chamber 75 (FIG. 9) of barrel 22. Rounded attachment guides 96, 98 are disposed forwardly of top and bottom rails 68, 69, respectively, and are configured to facilitate the assembly of frontal attachment 24 to front portion 64 of barrel 22 by passing above and below the arm connecting textured touch pad 46 to the back side of frontal attachment 24.

Referring to FIG. 7, annular opening 112 is provided in the back side of frontal attachment 24 to facilitate insertion of spring 50 and needle holder 52, discussed above in relation to FIG. 3, and spring 50 is desirably compressed between an annular shoulder inside front opening 42 (visible in FIG. 11) and is held in compression behind head 56 of needle holder 52 while frontal attachment 24 is moved into sliding engagement with front portion 64 of barrel 22. Frontal attachment 24 further comprises upper guide 44 having a downwardly facing, laterally extending recess 100 and lower guide 45 having an upwardly facing, laterally extending recess 102. Upper ramp and lower ramp 104, 106, respectively, of frontal attachment 24 are configured to slide over two laterally spaced-apart sets of opposed ramps with blocking shoulders 77, 79 (the lower set not being visible in FIG. 6). Laterally extending top rail 68 and bottom rail 69 of front portion 64 of barrel 22 are desirably cooperatively engaged with upper and lower recesses 100, 102, respectively, by sliding frontal attachment 24 onto front portion 64 of barrel 22 when frontal attachment 24 and front portion 64 are positioned as shown in FIG. 6. As pressure is applied to textured touch surface 46, frontal attachment 24 moves along rails 68, 69 until top and bottom blocking shoulders 108 of upper guide 44 pass over and then drops into facing relation to upper and lower blocking shoulders 77. At this time, needle support member 32 and needle holder 52 (not shown in FIGS. 6 and 7) are desirably coaxially aligned with the longitudinal axis of fluid chamber 75 (visible in FIG. 9). Any attempt to move frontal attachment 24 back to a disconnected position as shown in FIG. 6 will be resisted by facing and abutting contact between upper and lower blocking shoulders 77 of front portion 64 and top and bottom blocking shoulders 108, 110, respectively, of frontal attachment 24.

Figure 4:
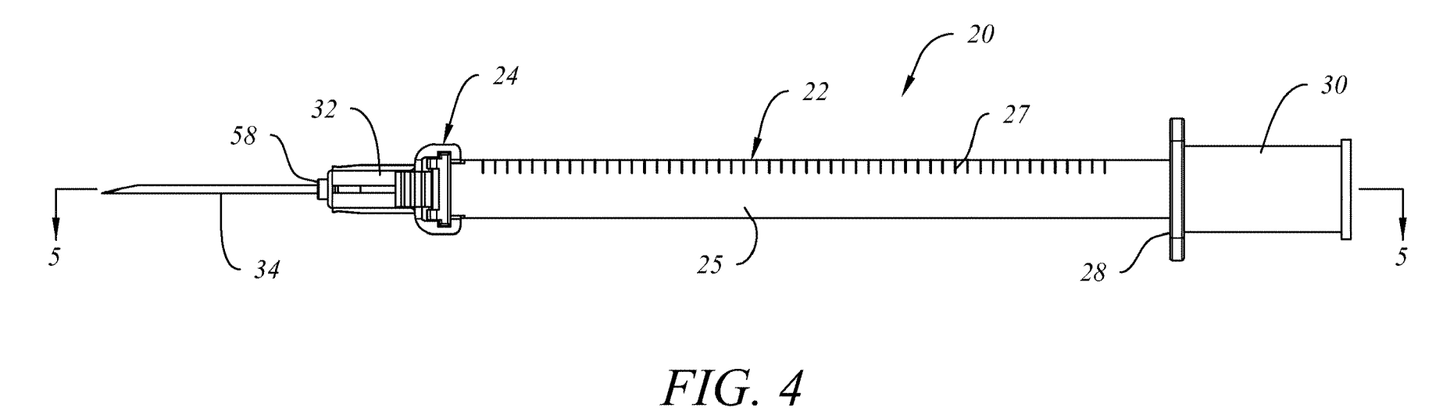
FIG. 4 is a right side elevation view of the embodiment of FIG. 2.
Figure 5:
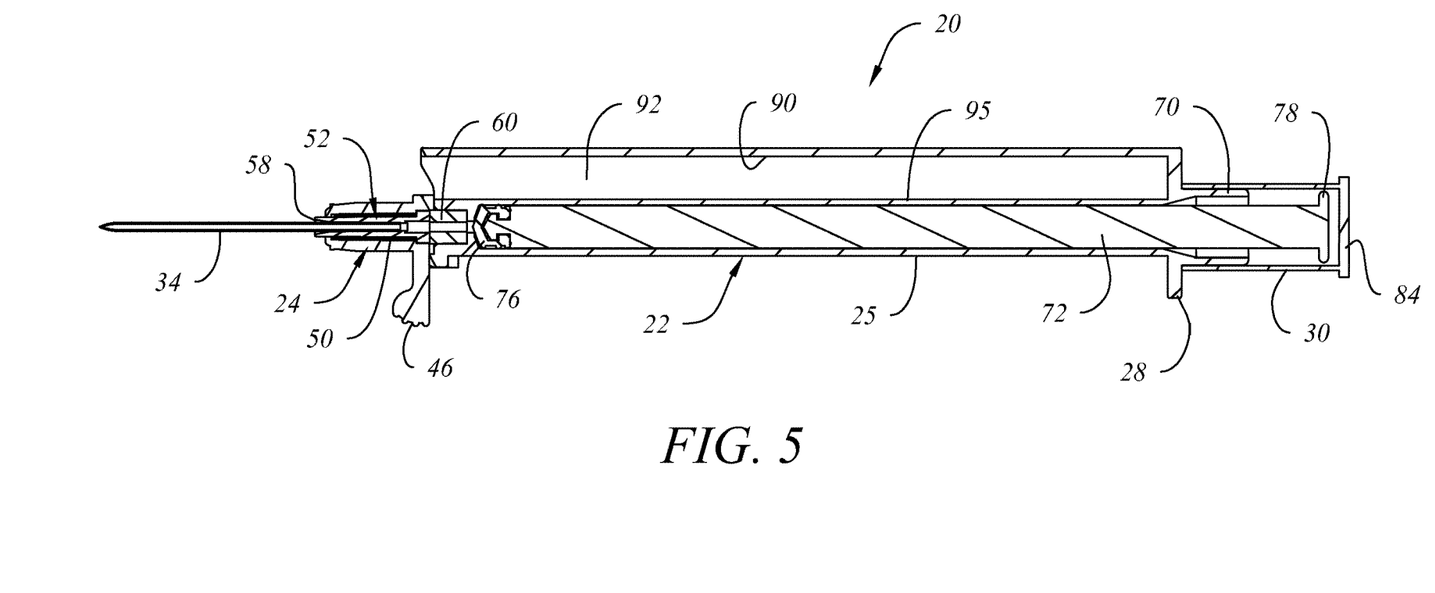
FIG. 5 is a cross-sectional view taken along line 5-5 of FIG. 4.

FIGS. 4 and 5 depict syringe 20 of FIG. 2 with the needle cover removed and with plunger cap 30 still in place and with textured touch surface 46 in the initial position relative to barrel 22 as described above. Needle 34 is installed inside bore 58 of needle holder 52, which is seated inside needle support member 32 of frontal attachment 24, with spring 50 compressed between head 56 (FIG. 3) of needle holder 52. Spring 50 applies a rearwardly directed biasing force to needle holder 52 and needle 34, and is pressed by spring 50 into facing and abutting contact with the front surface of annular fluid seal 60, thereby establishing a coaxially aligned fluid path through needle 34, needle holder 52 and fluid seal 60 into fluid chamber 75 (visible in FIG. 9) of barrel 22. As shown in FIGS. 4 and 5, plunger seal 76 is pushed fully forward into substantially cylindrical fluid chamber 75 of barrel 22.

Figure 8:
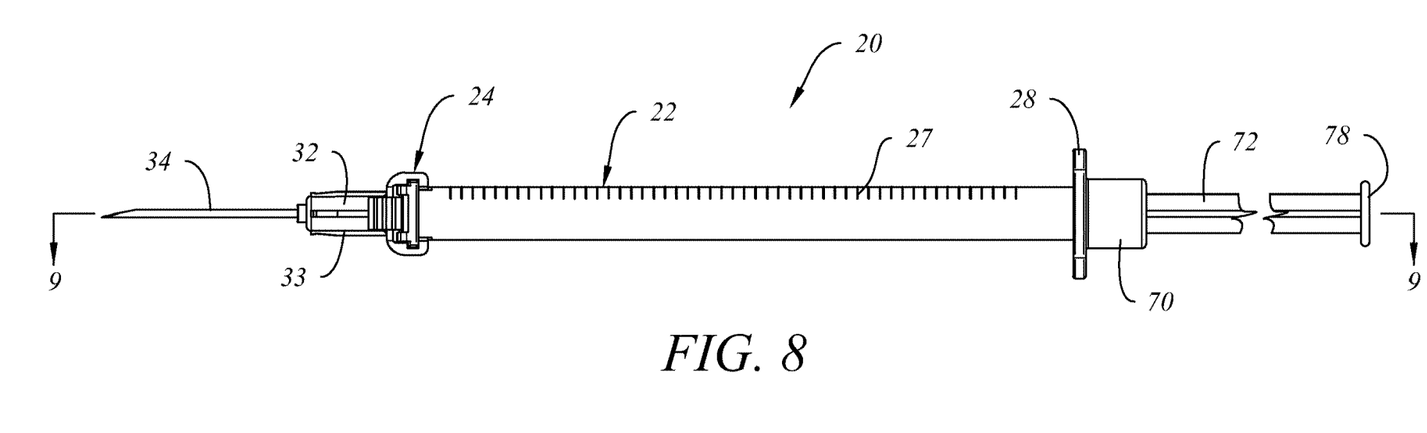
FIG. 8 is a right side elevation view of the embodiment of FIG. 4 with the plunger cap removed and with the plunger withdrawn to an aspirated position.

Referring to FIGS. 8-9, syringe 20 is configured so that fluid can be aspirated into the syringe, with textured touch pad 46 again in the same initial position as previously described. Plunger cap 30 (as seen in FIGS. 2, 4-5) is removed and plunger handle 72 is withdrawn as it would be while aspirating fluid into fluid chamber 75. In FIG. 9 it is seen that needle retraction cavity 92 is substantially coextensive in length with fluid chamber 75, thereby facilitating the placement of volumetric measuring indicia 27 on substantially flat surface 23 (visible in FIG. 3) that facilitates full utilization of the volume of fluid chamber 75 and also facilitating the retraction of needles such as biopsy needles that are often substantially longer than needle 34 (visible inside needle retraction cavity 92 in FIG. 11 below). Once fluid is aspirated into fluid chamber 75, fluid can also be injected into a patient or expelled from fluid chamber 75 by pressing forwardly on plunger thumb pad 78 while applying finger pressure against the forwardly facing side of flange 28.

Figure 10:
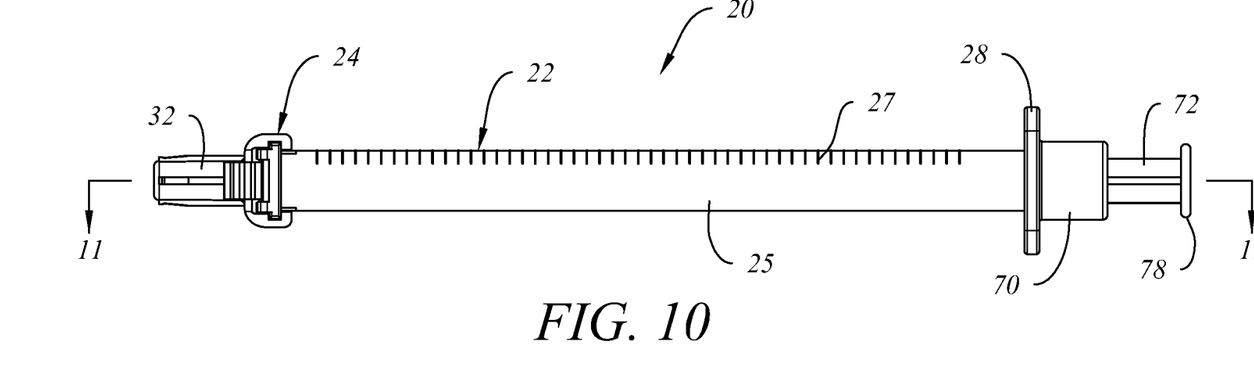
FIG. 10 is a right side elevation view of the embodiment of FIG. 8 with the needle retracted and with the plunger fully advanced inside the barrel.
Figure 13:
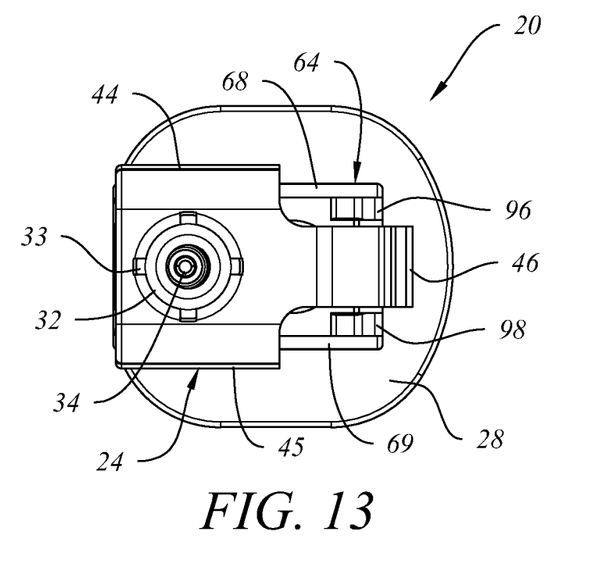
FIG. 13 is a front elevation view of the embodiment of FIG. 12 with the frontal attachment repositioned relative to the barrel and with the needle retracted to the position shown in FIGS. 10 and 11.

Referring to FIGS. 10-11 and 13, plunger handle 72 and plunger seal 76 have been pushed forwardly to empty fluid chamber 75. To initiate needle retraction, pressure is applied to textured touch pad 46, which moves frontal attachment to a position where needle support member 32 is aligned with needle retraction cavity 92. Because needle retraction chamber 92 has a front opening that is larger than head 56 of repositioned needle holder 52, the biasing force of compressed spring 52 pushes needle holder 52 rearwardly and causes needle holder 52 and needle 34 to be propelled into the distal end of needle retraction cavity 92.

Referring again to FIGS. 6 and 7, the further application of force to textured touch surface 46 of frontal attachment 24 relative to barrel 22 as described above in relation to FIGS. 10-11 produces sliding relative movement between frontal attachment 24 and front portion 64 of barrel 22. This movement causes upper ramp 104 and lower ramp 106 to slide over the second set of opposed ramps and blocking shoulders 79 so that top and bottom blocking shoulders 108, 110 are placed in facing and abutting contact with upper and lower blocking shoulders 79, thereby preventing frontal attachment 24 from being returned to the use position relative to barrel 22.

It will become apparent to those of ordinary skill in the art upon reading this specification in relation to the accompanying drawings that various other modifications and alterations can also be made to the embodiments disclosed here, and it is intended that the scope of the invention be limited only by the broadest interpretation of the appended claims to which the inventors are legally entitled.

We claim:
1. A syringe for medical use, comprising:
a barrel comprising (1) a proximal end, (2) a distal end, (3) a fluid chamber comprising a cylindrical sidewall, (4) a needle retraction cavity disposed parallel to, longitudinally coextensive with, and laterally offset and separated from the fluid chamber by a first portion of the cylindrical sidewall that provides the needle retraction cavity with a non-circular cross-section, and (5) an outer wall comprising a substantially flat indicia display portion;
a plunger configured to slidably engage with an interior surface of the cylindrical sidewall of the fluid chamber; and
a frontal attachment disposed at the proximal end of the barrel and comprising a retractable needle;
wherein the barrel is unitarily molded as one piece;
wherein the frontal attachment is configured to be slidably engageable with the proximal end of the barrel in a direction transverse to a longitudinal axis of the fluid chamber to move the retractable needle from a first position aligned with the fluid chamber prior to retraction of the retractable needle to a second position aligned with the needle retraction cavity to initiate retraction of the retractable needle upon actuation of the frontal attachment;
wherein the substantially flat indicia display portion is contiguous with and extends laterally in a single direction from a second portion of the cylindrical sidewall of the fluid chamber; and wherein an array of indicia comprising a volumetric dosage scale is disposed on the substantially flat indicia display portion.

2. The syringe of claim 1, wherein the substantially flat indicia display portion comprises two oppositely facing indicia display surfaces, with each indicia display surface being contiguous with and extending laterally in the single direction from the second portion of the cylindrical sidewall of the fluid chamber and forming at least a portion of an external wall of the needle retraction cavity;
wherein the volumetric dosage scale is applied to each indicia display surface and longitudinally aligned and coextensive in length with the fluid chamber.

3. The syringe of claim 1, wherein the plunger is coaxially aligned with the retractable needle when in the first position.

4. The syringe of claim 1, wherein the outer wall of the barrel further comprises the second portion of the cylindrical sidewall and a sidewall of the needle retraction cavity.

5. The syringe of claim 1, further comprising a removable needle cover, wherein the removable needle cover further comprises a locking member.

6. The syringe of claim 5, wherein the locking member is a locking arm extending into the needle retraction cavity.

7. The syringe of claim 1, further comprising a selectively removable plunger cap.

8. The syringe of claim 1, as configured for usable fluid volumes of 1 ml or less.

9. The syringe of claim 1, wherein the substantially flat indicia display portion is offset laterally towards the needle retraction cavity.

10. The syringe of claim 1, wherein the substantially flat indicia display portion is offset laterally from the longitudinal axis of the fluid chamber.

11. The syringe of claim 1, wherein the needle retraction cavity comprises at least one flat sidewall.

12. The syringe of claim 1, wherein the needle retraction cavity comprises an inwardly curved sidewall and wherein the inwardly curved sidewall is the first portion of the cylindrical sidewall of the fluid chamber.

13. The syringe of claim 12, wherein the needle retraction cavity comprises at least one flat sidewall coupled to the inwardly curved sidewall and wherein each of the at least one flat sidewall and the inwardly curved sidewall formed by the first portion of the cylindrical sidewall of the fluid chamber provide the needle retraction cavity with the non-circular cross-section.

14. The syringe of claim 1, wherein the substantially flat indicia display portion extends laterally from an end of the second portion of the cylindrical sidewall toward the needle retraction cavity and wherein the end is substantially aligned with the longitudinal axis of the fluid chamber.

15. The syringe of claim 1, wherein the substantially flat indicia display portion extends laterally beyond the first portion of the cylindrical sidewall and at least partially across a portion of each of the fluid chamber and the needle retraction cavity.

16. A medical syringe, comprising:
a one-piece barrel comprising a cylindrical fluid chamber, a non-cylindrical needle retraction cavity laterally spaced apart from and sharing a common interior wall with the cylindrical fluid chamber, and a flat indicia display extending across the common interior wall and over at least a portion of the cylindrical fluid chamber and at least a portion of the non-cylindrical needle retraction cavity;
a needle that projects forwardly from the one-piece barrel when in an injection position communicating with the cylindrical fluid chamber to establish a coaxially aligned fluid flow path between the cylindrical fluid chamber and the needle; and
a retraction actuator disposed at a forward end of the one-piece barrel and comprising an arm that extends laterally beyond an outer edge of the one-piece barrel, the retraction actuator slidably engageable with the barrel to initiate retraction of the needle into the needle retraction cavity upon application of pressure on a distal end of the arm; and
wherein the flat indicia display does not extend over the distal end of the arm.

17. The medical syringe of claim 16, further comprising a frontal attachment slidably engaging a distal end of the one-piece barrel in a direction transverse to a longitudinal axis of the cylindrical fluid chamber, the frontal attachment being selectively repositionable by a user to interrupt the coaxially aligned fluid flow path following an injection and to move the needle into alignment with the needle retraction cavity.

18. The medical syringe of claim 16, wherein the flat indicia display further comprises an array of indicia comprising a volumetric dosage scale.

19. A medical syringe, comprising:
a one-piece barrel comprising (1) an upper wall, (2) a lower wall, (3) a first curved sidewall, (4) a second sidewall, (5) a curved inner wall in direct contact with the upper wall and the lower wall, (6) a cylindrical fluid chamber partially formed by the first curved sidewall and the curved inner wall, and (7) a needle retraction cavity formed by a portion of the upper wall, a portion of the lower wall, the second sidewall, and the curved inner wall, wherein the curved inner wall separates the cylindrical fluid chamber from the needle retraction cavity to provide the cylindrical fluid chamber with a circular cross-sectional shape and provide the needle retraction cavity with a non-circular cross-sectional shape;
a needle projecting forwardly from the one-piece barrel in coaxial alignment with the cylindrical fluid chamber;
a volumetric scale at least partially disposed on a substantially flat surface, wherein the substantially flat surface is longitudinally coextensive with and contiguous to each of the first curved sidewall and the second sidewall, overlies a portion of the cylindrical fluid chamber to permit direct viewing by a user of a medicinal fluid drawn into the cylindrical fluid chamber through the needle, and overlies a portion of the needle retraction cavity to allow viewing of the needle after retraction of the needle, wherein at least one of the upper wall and the lower wall comprises the substantially flat surface.

20. A medical syringe useful for administering an injection of medicinal fluid, comprising:
a transparent one-piece barrel comprising (1) an inwardly facing curved wall defining at least a first portion of a cylindrical fluid chamber and at least a first portion of a needle retraction cavity to provide the needle retraction cavity with a non-circular cross-sectional shape, (2) an outwardly facing wall section unitarily molded together with the inwardly facing wall, the outwardly facing wall section comprising a substantially flat portion that extends laterally across the inwardly facing wall and overlies in direct contact with at least a second portion of the cylindrical fluid chamber and at least a second portion of the needle retraction cavity, and (3) a volumetric scale comprising numeric indicia;

a plunger handle with a plunger seal slidably engaging the inwardly facing wall; and
a forwardly projecting needle coaxially aligned with the cylindrical fluid chamber to establish a coaxially aligned fluid flow path between the cylindrical fluid chamber and the forwardly projecting needle;
wherein at least a portion of the volumetric scale is disposed on the substantially flat portion to allow a user of the medical syringe to view the plunger seal and to view a medicinal fluid drawn into any portion of the cylindrical fluid chamber directly through the inwardly facing wall defining the cylindrical fluid chamber.

21. The medical syringe of claim 20, wherein the needle retraction cavity is parallel to, offset laterally from, and longitudinally coextensive with the cylindrical fluid chamber, wherein the needle retraction cavity comprises an open distal end configured to receive the forwardly projecting needle following an injection.

22. The medical syringe of claim 21, further comprising a frontal attachment slidably engaging a distal end of the one-piece barrel in a direction transverse to a longitudinal axis of the cylindrical fluid chamber, the frontal attachment comprising a tubular needle support member configured to support the forwardly projecting needle in rearwardly biased, coaxial alignment with the cylindrical fluid chamber prior to and during use of the medical syringe for administering an injection.

23. The medical syringe of claim 22, wherein the frontal attachment is selectively repositionable laterally relative to the one-piece barrel following an injection to align the rearwardly biased, forwardly projecting needle with the open distal end of the needle retraction cavity to initiate retraction of the forwardly projecting needle into the needle retraction cavity of the one-piece barrel.

24. The medical syringe of claim 20, wherein the substantially flat portion comprises a first flat indicia display surface, the medical syringe further comprising a second flat indicia display surface oppositely facing from the first flat indicia display surface, with the first flat indicia display surface facing outwardly from a first side of the cylindrical fluid chamber of the transparent one-piece barrel and the second flat indicia display surface facing outwardly from a second side of the cylindrical fluid chamber of the transparent one-piece barrel that is opposite from the first side.

25. The medical syringe of claim 21, wherein the substantially flat portion comprises a first flat indicia display surface, the medical syringe further comprising a second flat indicia display surface oppositely facing from the first flat indicia display surface, with the first flat indicia display surface facing outwardly from a first side of the needle retraction cavity and the second flat indicia display surface facing outwardly from a second side of the needle retraction cavity that is opposite from the first side.

26. A barrel for a medical syringe, the barrel comprising:
a fluid chamber having an interior surface that is circular in cross-section;
a needle retraction cavity having (1) an interior surface that is non-circular in cross-section, (2) a first substantially flat sidewall, (3) a second substantially flat sidewall, and (4) an interior curved sidewall, wherein the interior curved sidewall is common to the fluid chamber, is curved inwardly towards the needle retraction cavity, and separates the fluid chamber from the needle retraction cavity to at least partially form the interior surface of the needle retraction cavity that is non-circular in cross-section;
an outer wall comprising the first substantially flat sidewall, the second substantially flat sidewall, and a curved wall that forms an outer surface of a part of the fluid chamber, wherein each of the first substantially flat sidewall and the second substantially flat sidewall extends laterally over a portion of each of the fluid chamber and the needle retraction cavity and across the interior curved sidewall, and wherein each of the first substantially flat sidewall and the second substantially flat sidewall is contiguous with the curved wall; and
at least one indicia display disposed on the first substantially flat sidewall; and
a needle retraction actuator slidably engaged with the barrel and configured to reposition a retractable needle from a first position in which the retractable needle is aligned with the fluid chamber to a second position in which the retractable needle is aligned with the needle retraction cavity to initiate retraction of the retractable needle into the needle retraction cavity.

27. The medical syringe of claim 26, comprising a first indicia display and a second indicia display;
wherein the first indicia display is disposed on a first substantially flat portion of the outer wall;
wherein the second indicia display is disposed on a second substantially flat portion of the outer wall; and
wherein the first substantially flat portion of the outer wall is oppositely facing from the second substantially flat portion of the outer wall.

28. The medical syringe of claim 26, further comprising a volumetric scale disposed on the at least one indicia display, wherein at least part of the volumetric scale overlies a part of the fluid chamber.

29. The barrel of claim 26, wherein the outer wall comprises a curved wall, a substantially flat upper wall, a substantially flat lower wall, and a fourth wall substantially opposite the curved wall;
wherein the at least one indicia display is disposed on the substantially flat upper wall or the substantially flat lower wall or both;
wherein the curved wall forms part of the fluid chamber; and
wherein the fourth wall forms part of the needle retraction cavity.

30. The barrel of claim 29, wherein a first portion of the substantially flat upper wall and a first portion of the substantially flat lower wall form the first substantially flat sidewall and the second substantially flat sidewall of the needle retraction cavity.

31. The barrel of claim 29, wherein a second portion of the substantially flat upper wall and a second portion of the substantially flat lower wall are disposed in contact with portions of the fluid chamber.

32. The barrel of claim 26, wherein the needle retraction cavity is longitudinally coextensive with the fluid chamber.

33. The barrel of claim 26, wherein each of the first substantially flat sidewall and the second substantially flat sidewall of the outer wall is continuous with and extends laterally from the curved wall.

34. The barrel of claim 33, wherein each of the first substantially flat sidewall and the second substantially flat sidewall of the outer wall extends laterally in a single direction relative to the curved wall.

35. The barrel of claim 34, wherein the single direction is in a direction of curvature of the curved wall.

36. The barrel of claim 34, wherein the curved wall forms part of the fluid chamber.

37. The barrel of claim 36, wherein at least a portion of the at least one indicia display is disposed on the curved wall and wherein the at least one indicia display comprises a volumetric scale.

38. The barrel of claim 26, wherein the at least one indicia display is wider than the fluid chamber and longitudinally contiguous with the fluid chamber.

39. The barrel of claim 26, wherein the at least one indicia display is not wider than a width of the fluid chamber and the needle retraction cavity combined.

40. A medical syringe, comprising:
a barrel comprising a substantially flat outer wall that overlies at least portion of a cylindrical fluid chamber having a circular cross-section and a needle retraction chamber having a non-circular cross-section that is defined at least partially by a common wall shared between the cylindrical fluid chamber and the needle retraction chamber;
a needle retraction actuator slidably engaged with the barrel and configured to reposition a retractable needle from a first position in which the retractable needle is aligned with the cylindrical fluid chamber to a second position in which the retractable needle is aligned with the needle retraction chamber to initiate retraction of the retractable needle into the needle retraction chamber; and
a volumetric scale disposed on the substantially flat outer wall;
wherein the barrel is unitarily molded as a single piece;
wherein the barrel and volumetric scale are configured to allow a user to directly view a fluid within the cylindrical fluid chamber through the substantially flat outer wall and to simultaneously view the fluid and the volumetric scale; and
wherein the cylindrical fluid chamber is configured for a useable fluid volume of 1 mL or less.

41. A medical syringe, comprising:
a barrel comprising a curved surface and a substantially flat surface that is contiguous with the curved surface and extends laterally from an end of the curved surface at least partially across each of a cylindrical fluid chamber and a needle retraction chamber that are divided by a common curved interior wall that intersects the substantially flat surface and provides the cylindrical fluid chamber with a circular cross-section and the needle retraction chamber with a non-circular cross-section;
a volumetric scale disposed on the substantially flat surface; and
a needle retraction actuator slidably engaged with the barrel and configured to reposition a retractable needle from a first position in which the retractable needle is aligned with the cylindrical fluid chamber to a second position in which the retractable needle is aligned with the needle retraction chamber to initiate retraction of the retractable needle into the needle retraction chamber.

* * * * *